Feb. 10, 1953 E. S. BOERNER Plant Pat. 1,166
CHRYSANTHEMUM PLANT
Filed April 21, 1952
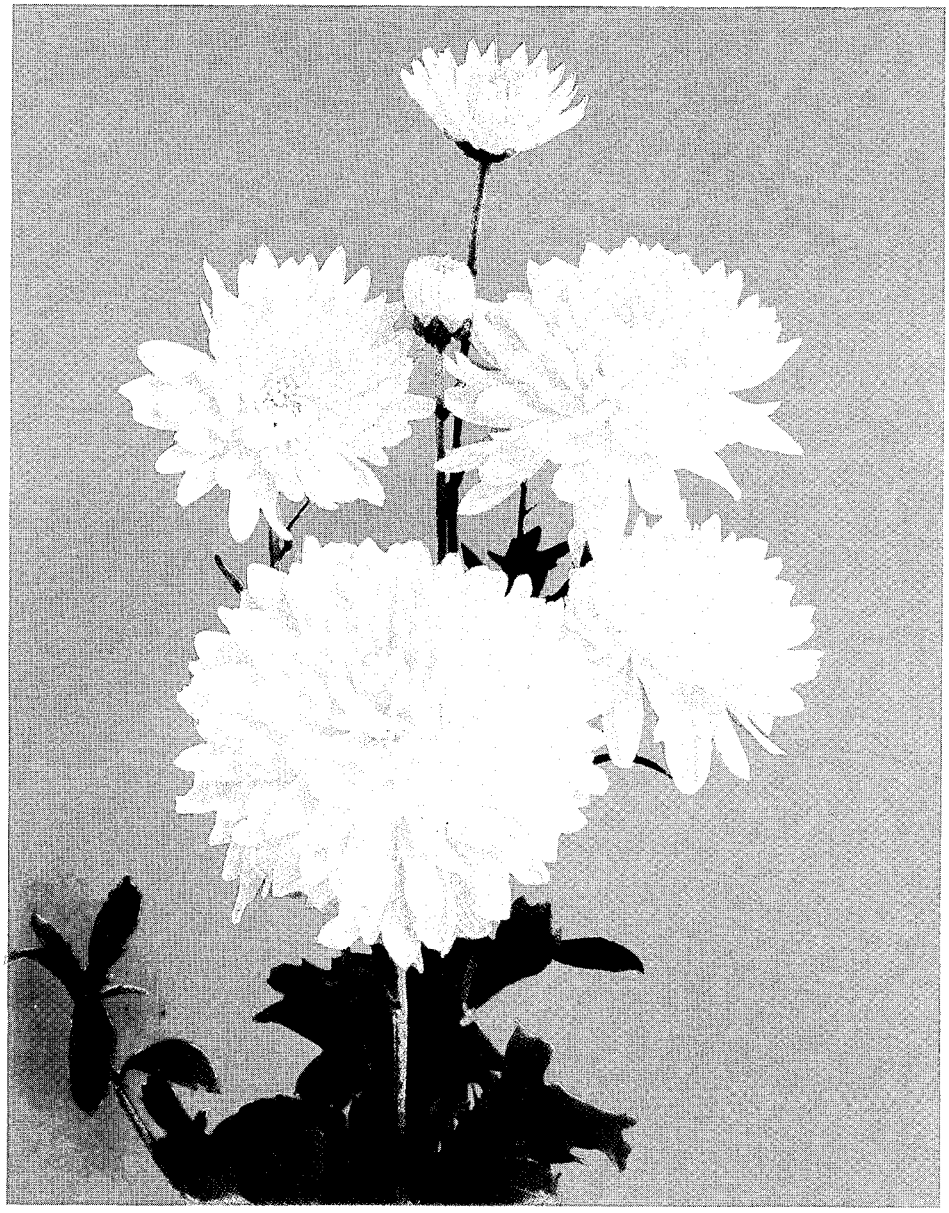
Inventor.
E. S. Boerner
By: Robert Cobb
Attorneys.

Patented Feb. 10, 1953

Plant Pat. 1,166

UNITED STATES PATENT OFFICE 1,166

CHRYSANTHEMUM PLANT

Eugene S. Boerner, Newark, N. Y., assignor to Jackson & Perkins Company, Newark, N. Y., a corporation of New York Application April 21, 1952, Serial No. 283,374

1 Claim. (Cl. 47—60)

The present invention relates to a new and distinct variety of chrysanthemum plant that was originated by me by crossing an unnamed and unpatented hardy, large-flowered yellow chrysanthemum of the greenhouse type with an unnamed and unpatented seedling that is identified in my breeding records by #4432-1 and which originated as a cross of a hardy, dwarf yellow seedling × "Algonquin" (unpatented), the latter variety being an early flowering yellow chrysanthemum.

The primary objective of this cross was to breed hardiness and frost-resistance into the large greenhouse type aforementioned, and also to attain an early blooming characteristic so that the variety would bloom outdoors under these climatic conditions. These objectives were fully achieved in my new variety, with respect to its earliness of bloom and the hardiness and frost-resistance of the plant, as evidenced by the following outstanding characteristics which distinguish the new variety from its parents, as well as from all other varieties of which I am aware:

(1) The production of larger flowered blooms on straight, upright growth;

(2) Improved frost-resistance of the large-sized flowers; and (3) The general color tonality of the flowers which may be characterized as Empire Yellow, and which is distinctive from all other chrysanthemums.

Asexual reproduction of this new variety by both top cuttings and by underground runners, in the fields, at Newark, New York, shows that the foregoing characteristics and distinctions come true to form and are established and transmitted through succeeding propagations.

The accompanying drawing shows specimens of my new chrysanthemum variety, with the flowers and foliage in different stages of development.

The following is a detailed description of the new variety, as observed in the fields at Newark, New York, in the latter part of the month of September and about at mid-morning, with color terminology in accordance with Ridgway's Color Standards and Nomenclature:

Parentage: An unnamed hardy, large-flowered yellow chrysanthemum of the greenhouse type × an unnamed variety #4432-1 (a hardy, dwarf yellow seedling × "Algonquin").

Classification: Incurved type.

Growth: Upright, straight growth, similar to greenhouse varieties; attains a height of 3 ft. to 3½ ft.

Cold resistance: Very hardy; very frost-resistant petals, as determined by comparison with other varieties grown under comparable conditions.

Blooming period: In Newark, New York, climatic area, date of start of bloom is about September 15th, and the plant is very free blooming until severe freezing in October and November.

Bud:

*Color.*—When sepals first divide—Pale Lemon Yellow, Plate 4. When petals begin to unfurl—Empire Yellow, Plate 4. When half blown—inside of petals: Lemon Yellow, Plate 4; reverse of petals: Picric Yellow, Plate 4.

*Peduncle.*—Color—Light Cress Green, Plate 31. Strength—strong.

Bloom:

*Size.*—4 inches to 4½ inches.

*Stem.*—Strong; normal.

*Form.*—Incurved.

*Petalage.*—Double.

*Color.*—Center of flower—Empire Yellow, Plate 4. Outer petals—Pale Lemon Yellow, Plate 4. Base of petals—Light Lumiere Green, Plate 17. Inside of petals—Pale Lemon Yellow, Plate 4. Reverse of petals—Picric Yellow, Plate 4.

*Petals.*—Texture—medium. Form—oval.

Fragrance: Characteristic chrysanthemum.

Plant:

*Form.*—Upright; compact.

*Growth.*—Free.

Foliage:

*Size.*—Medium.

*Quantity.*—Normal.

*Color.*—Upper side—Dark Cress Green, Plate 31; reverse side—Bice Green, Plate 17.

*Texture.*—Leathery.

I claim:

A new and distinct variety of chrysanthemum plant of the incurved type, substantially as herein shown and described, characterized particularly as to novelty by its large-flowered blooms on straight, upright growth, by the improved frost-resistance of the large-sized flowers, by the distinctive Empire Yellow general color tonality of its flowers, and by its hardiness and early blooming habits of growth.

EUGENE S. BOERNER.

No references cited.